United States Patent [19]
Fergason

[11] Patent Number: 5,959,705
[45] Date of Patent: Sep. 28, 1999

[54] WELDING LENS WITH INTEGRATED DISPLAY, SWITCHING MECHANISM AND METHOD

[75] Inventor: John D. Fergason, Mountainview, Calif.

[73] Assignee: OSD Envizion, Inc., Menlo Park, Calif.

[21] Appl. No.: 08/623,972

[22] Filed: Mar. 29, 1996

Related U.S. Application Data

[63] Continuation-in-part of application No. 08/616,264, Mar. 15, 1996.

[51] Int. Cl.$^6$ .......................................................... G02F 1/133
[52] U.S. Cl. ............................. 349/14; 349/142; 349/149; 349/58; 2/8
[58] Field of Search ................................. 349/13, 58, 14, 349/149, 8, 81, 142; 219/147; 2/8; 351/45, 49; 200/237; 345/7

[56] References Cited

U.S. PATENT DOCUMENTS

| | | |
|---|---|---|
| Re. 29,684 | 6/1978 | Gordon . |
| Re. 32,521 | 10/1987 | Fergason . |
| D. 349,588 | 8/1994 | Howard et al. . |
| D. 353,692 | 12/1994 | Fergason et al. . |
| 3,731,986 | 5/1973 | Fergason . |
| 3,881,809 | 5/1975 | Fergason et al. . |
| 4,039,254 | 8/1977 | Harsch . |
| 4,385,806 | 5/1983 | Fergason . |
| 4,436,376 | 3/1984 | Fergason . |
| 4,540,243 | 9/1985 | Fergason . |
| 4,582,396 | 4/1986 | Bos et al. . |
| 4,882,769 | 11/1989 | Gallimore ................................. 455/344 |
| 5,074,647 | 12/1991 | Fergason et al. . |
| 5,208,688 | 5/1993 | Fergason et al. . |
| 5,248,880 | 9/1993 | Fergason . |
| 5,252,817 | 10/1993 | Fergason et al. . |
| 5,347,383 | 9/1994 | Fergason . |
| 5,377,032 | 12/1994 | Fergason et al. . |
| 5,671,035 | 9/1997 | Barnes ....................................... 351/45 |

*Primary Examiner*—Hung Xuan Dang
*Assistant Examiner*—Tai V. Duong
*Attorney, Agent, or Firm*—Howell & Haferkamp, L.C.

[57] ABSTRACT

A switch activating system for an automatically darkening lens system and an automatically darkening lens system including such a switch activating system, includes a cover plate through at least part of which a scene may be viewed, a support, a pair of switch electrodes, one switch electrode positioned in relatively fixed relation with said support, the other switch electrode being positioned for movement with respect to said one switch electrode selectively to make electrical connection therewith in response to deflecting of said cover plate. The automatically darkening lens assembly also includes a controllable light shutter for controlling transmission of light for viewing therethrough, and a circuit for operating said light shutter and affecting operating characteristics thereof. A method for operating an auto-darkening welding lens including an operating circuit includes selecting an operational characteristic of the welding lens by setting a characteristic of the circuit, said setting comprising deflecting a mechanical member of the welding lens to operate a switch.

20 Claims, 3 Drawing Sheets

FIG. 4 NON ACTIVATED SWITCH

FIG. 5 ACTIVATED SWITCH

WELDING LENS WITH INTEGRATED DISPLAY, SWITCHING MECHANISM AND METHOD

This is a continuation-in-part of copending U.S. patent application Ser. No. 08/616,264, filed Mar. 15, 1996, entitled "Welding Lens With Integrated Display And Method".

TECHNICAL FIELD

The present invention relates generally, as is indicated, to an indicator system for a light shutter or the like, and, more particularly, to an automatic welding lens with an integral display or indicator to display various operative characteristics of the welding lens and to a method for protecting the eyes.

The present invention also relates generally to the control of transmission of electromagnetic energy, such as light in the visible, infrared and/or ultraviolet wavelength ranges, and, more particularly, the present invention relates to improvements for displaying the operative mode of an automatically controlled eye protection device, such as a welding helmet or lens for a welding helmet or the like.

Further, the present invention relates to a light shutter switch assembly which includes an integrated switching mechanism for controlling one or more operating modes or operational characteristics of the light shutter.

BACKGROUND

In the following description reference will be made to a lens, especially to an automatically darkening lens that is able to operate automatically to control transmission of light. The lens may be a light shutter type of a device that is able to control light transmission without distorting, or at least with relatively minimal distortion, of the light and the image characteristics carried by the light or represented by the light. Therefore, when a person looks through the lens, the image seen would be substantially the same as the image seen without the lens, except that the intensity of the light transmitted through the lens may be altered depending on the operative state of the lens. The lens may be used in a welding helmet, and the lens may be used in other types of devices, such as goggles, face masks, other types of helmets, etc. Such devices usually are employed to protect the face or the eyes of a person, as is known, for example, in the field of welding and in other fields, too.

For the purposes of providing eye protection, usually a welding lens provides light blocking characteristics in the visible, infrared and ultraviolet wavelength ranges. The actual ranges may be determined by the components of the lens, the arrangement of those components, and so forth. One example of a lens useful in accordance with the present invention is disclosed in copending, commonly owned U.S. patent application Ser. No. 08/105,734, filed Aug. 11, 1993, the entire disclosure of which hereby is incorporated by reference. The lens assembly disclosed in that patent application includes several liquid crystal cell light shutters, several plane polarizers, and a reflector or band pass filter, which is able to reflect ultraviolet and infrared electromagnetic energy and possibly also some electromagnetic energy in the visible wavelength range. The several liquid crystal cells, for example, may be birefringent liquid crystal cells sometimes referred to as surface mode liquid crystal cells or pi-cells.

Examples of liquid crystal cells, lenses using them and drive circuits are described in U.S. Pat. Nos. 5,208,688, 5,252,817, 5,248,880, 5,347,383, and 5,074,647 and in pending U.S. patent application Ser. No. 08/027,385 filed Feb. 17, 1993. In U.S. Pat. No. 5,074,647, several different types of variable polarizer liquid crystal devices are disclosed. Twisted nematic liquid crystal cells used in an automatic shutter for welding helmets are disclosed in U.S. Pat. Nos. 4,039,254 and Re. 29,684. Exemplary birefringent liquid crystal cells useful as light shutters in the present invention are disclosed in U.S. Pat. Nos. 4,385,806, 4,436,376, 4,540,243, 4,582,396, and Re. 32,521 and exemplary twisted nematic liquid crystal cells and displays are disclosed in U.S. Pat. Nos. 3,731,986 and 3,881,809. The entire disclosures of the patents and applications mentioned herein are incorporated by reference.

As is disclosed in several of the above patents, the respective shutters may have one or more operational characteristics (sometimes referred to as modes or states). One example of such an operational characteristic is the shade number; this is the darkness level or value of the shutter when it is in the light blocking mode. Another exemplary operational characteristic is the delay time during which the shutter remains in a dark state after a condition calling for the dark state, such as detection of the bright light occurring during welding, has ceased or detection thereof has terminated or been interrupted. Still another operational characteristic is sensitivity of the detection circuit and/or shutter to incident light, for example, to distinguish between ambient conditions and the bright light condition occurring during a welding operation. Even another characteristic, which may be considered an operational characteristic, is the condition of the battery or other power source for the shutter, such as the amount of power remaining, operational time remaining until the power source becomes ineffective, etc. In the past various of the operational characteristics of such shutters have been adjustable or fixed. However, relatively large devices were used to adjust and to display the values or settings of such operational characteristics, as by dials or knobs. It would be desirable to reduce the space required for such components and to improve the operability of them. It would be desirable to minimize the size and weight of such control and display components thereby to minimize size and weight of a welding lens or other automatic shutter device. Further, it would be desirable to facilitate manufacturing such automatic shutters.

An example of a "welding lens with integrated display and method" is disclosed in copending, commonly owned U.S. patent application Serial. No. (Express Mail No. EM402013379US), filed Mar. 15, 1996. In the invention disclosed therein the current operational characteristics of the shutter can be displayed and can be selectively changed by operating one or more switches. The switches may be flexible membrane switches, microswitches, or another type of switch. It is desirable to reduce the size of the switches, space required in the shutter assembly for the switches and weight of the shutter assembly.

A cover lens, sometimes referred to as a cover plate, is useful for protecting the light shutter, and especially the liquid crystal cell thereof, in addition to the eyes of the user. For example, the cover lens protects the light shutter from damage or dirt due to contact with fingers, etc. A cover lens may be included in the welding helmet lens aperture in front of and/or behind the light shutter. In the event the cover lens itself becomes damaged, scratched, dirty, etc., it usually may be replaced relatively easily.

The present invention is particularly useful for eye protection by an automatic darkening light shutter in a helmet or goggle assembly or in another device, if desired. The switching mechanism for powering the light shutter on and off and/or for selecting operational characteristics is an integral part of the light shutter and/or frame assembly or other component or portion thereof.

The light shutter of the present invention may be used in a variety of embodiments and applications. The shutter is adjustable to control light, i.e., to increase or to decrease the amount of the incident light which is transmitted through the shutter. When welding is not occurring, for example, the shutter in a welding helmet may be substantially optically clear or transmissive or at least minimizes its attenuation of light. When welding is occurring, the shutter may be dark or closed to reduce the amount of light transmitted therethrough in order to protect the eyes of the person performing the welding and maximize his or her viewing comfort. In both cases, though, the image characteristics of the light preferably remain intact. A photosensitive device may be used to sense the intensity of light impinging in the area of the shutter so as to provide an input to a drive circuit for the shutter in order to control opening and closing thereof.

An example of a "welding lens with integrated display and method" is disclosed in copending, commonly owned U.S. patent application Serial. No. (Express Mail No. EM402013379US), filed Mar. 15, 1996.

The disclosures of the patents and patent applications identified herein are specifically incorporated in their entirety by reference.

SUMMARY

With the foregoing in mind, then, one aspect of the present invention relates to a switch activating system for a lens system, including a cover plate through at least part of which a scene may be viewed, a support, a pair of switch electrodes, one switch electrode positioned in relatively fixed relation with said support, the other switch electrode being positioned for movement with respect to said one switch electrode selectively to make electrical connection therewith in response to deflecting of said cover plate.

Another aspect relates to a switch for an electrical device, including a support substrate on which electrical circuitry is located, a plurality of switch electrodes relatively in fixed positional relation with respect to said support substrate, a switch pad for selective movement with respect to said plurality of switch electrodes to effect electrical connection of a plurality of said electrodes, a flexible mount for mounting said switch pad in overlying spaced relation to said plurality of switch electrodes, and a spacer for spacing said flexible mount and switch pad in such spaced overlying relation, said switch pad being movable to connect plural switch electrodes upon flexing of said flexible mount to urge the switch pad into engagement with said switch electrodes.

A further aspect relates to an automatically darkening lens assembly, including a controllable light shutter for controlling transmission of light for viewing therethrough, a circuit for operating said light shutter and affecting operating characteristics thereof, a switch operable to select at least one of such operating characteristics, a support for mounting at least a portion of said switch, a cover plate overlying at least part of said light shutter and said circuit, said switch being operable in response to deflection of said cover plate.

An additional aspect relates to a light shutter for a welding helmet, including a frame structure for an electro-optic shutter assembly, said frame structure having front surface to be exposed to light and a back surface facing a viewer during welding operation, a protective member covering at least a part of the back surface, switching means for controlling an operational mode of said electro-optic shutter assembly, said switching means being operable in response to pressure applied to said protective member.

Another aspect relates to a switch arrangement for a light shutter and an indicator arrangement (sometimes referred to as a display) for the light shutter or the like wherein the indicator is integral with the shutter for indicating an operational characteristic thereof.

Another aspect relates to an automatic darkening welding lens assembly in which an indicator is integral with the welding lens assembly and is viewable when the welding lens assembly is not in the dark protective mode and is not viewable and does not interfere with eye protection when the welding lens assembly is in dark mode.

These and other objects, features, advantages and functions of the invention will become more apparent as the following description proceeds.

It will be appreciated that although the invention is described with respect to a preferred embodiment, the scope of the invention is limited only by the claims and equivalents thereof. Also, although the invention is described with respect to a liquid crystal light shutter used in a welding helmet for eye protection therein, it will be appreciated that the various features of the invention may be used in conjunction with other devices and functions.

To the accomplishment of the foregoing and related ends, the invention, then, comprises the features hereinafter described in the specification and particularly pointed out in the claims, the following description and the annexed drawings setting forth in detail certain illustrative embodiments of the invention, these being indicative, however, of but several of the various ways in which the principles of the invention may be suitably employed.

DESCRIPTION

Figures 1, 2, 3, 4, 5:
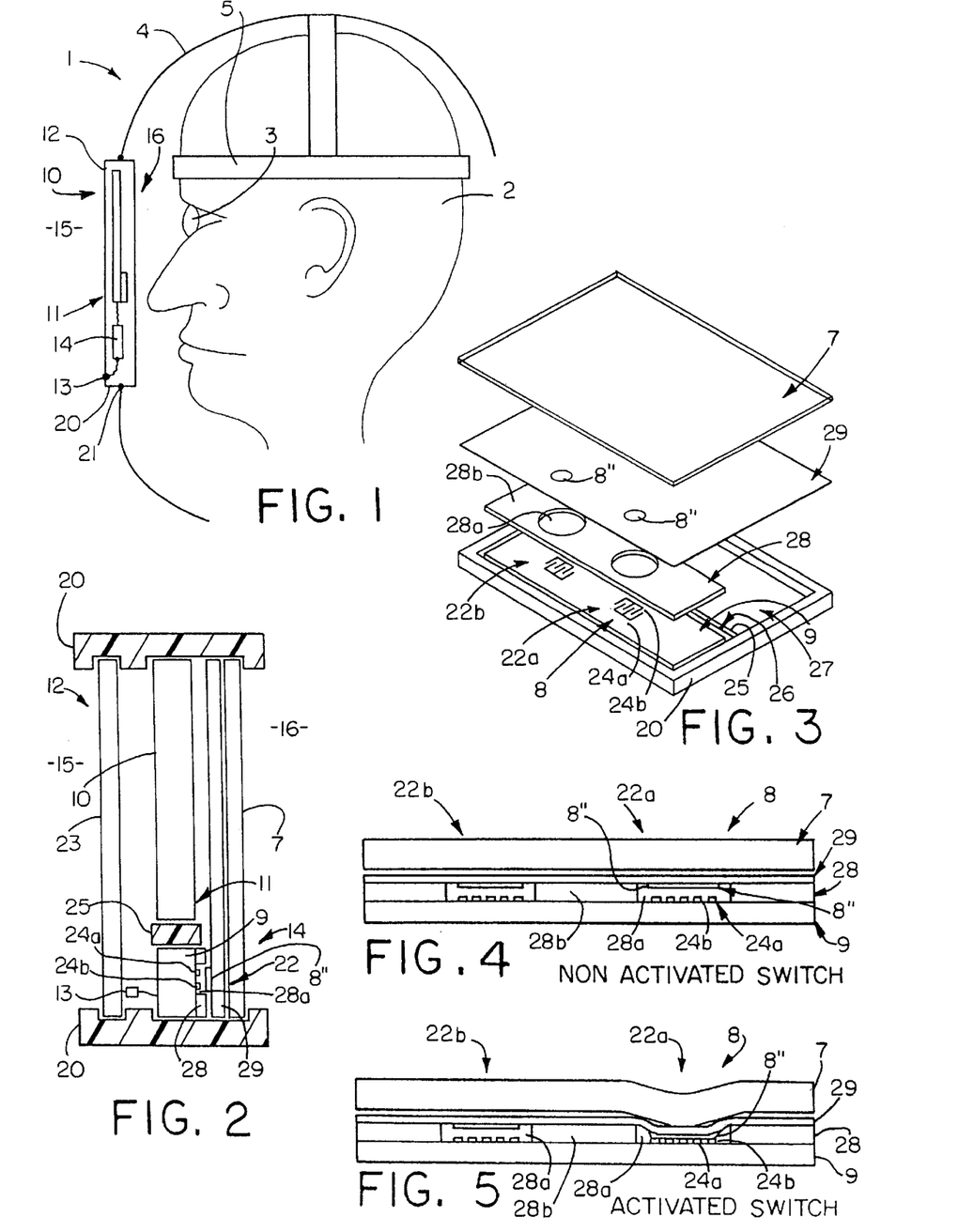
FIG. 1 is a schematic illustration of a welding helmet including a welding lens assembly with an automatic shutter and an integral indicator or display, the helmet being positioned on the head of an individual, such as a welder.
FIG. 2 is a schematic side elevation view, partly shown in section, of the welding lens cartridge assembly of the invention.
FIG. 3 is an exploded isometric view of a switching mechanism of the invention.
FIGS. 4 and 5 are fragmentary section views of the switching mechanism in accordance with the invention, shown, respectively, in unactivated and activated (pressed) conditions.

Referring in detail to the drawings, wherein like reference numerals designate like parts in the several figures, and initially to FIGS. 1–3, there is illustrated a welding helmet 1 worn on the head of a person 2 to protect the person's eyes 3 from light generated during welding operation or some other operation in which eye protection from bright light is desired. The welding helmet 1 includes a shell 4, which provides physical protection for the person 2 from sparks, molten metal, small scattering debris, and the like, and a head gear 5, such as a mounting band or the like, for mounting the helmet on the head of the person 2. The welding helmet 1 may be a separate device or it may be part of a further assembly, such as a structure that provides air for breathing by the person 2, other ventilating equipment, etc.

A switch system 6, including a deflectable cover plate 7, switch electrodes 8, and a support 9, is associated with an automatic light shutter 10. To permit viewing by the person's eyes 3, when the welding helmet 1 is worn, the welding helmet 1 includes the automatic light shutter 10 in a position for the eyes to look through. An integral indicator 11 associated with the shutter 10 displays operative conditions of the shutter, such as those conditions set by operating the switch system 6. The shutter, switch system and indicator are supported in a welding lens cartridge assembly 12 that is secured in the shell 4.

The shutter 10 is an automatic shutter able to be operated in a clear state or a dark state (and possibly also in one or more intermediate states) in response to lighting conditions detected by a sensor 13 which is coupled to operating or driving circuitry 14. In the embodiment described herein the shutter 10 includes plural liquid crystal cells which are operated by the circuitry 14 so that the shutter 10 selectively assumes the clear or light transmitting state or assumes the dark or light blocking state, depending on conditions detected by the sensor 13 and operation of the circuitry 14. Shutters, sensors and circuitry generally of the type described herein also are described in various of the above patents and applications.

In the clear state the shutter 10 transmits to the eyes 3 a relative maximum amount of light from outside the helmet to permit viewing of a welding location, tools for use in welding, a part being welding, etc. Being able to view the welding site, for example, facilitates the setting up of the welding tools so that the person can commence welding in an efficient and safe manner. When the sensor 13 detects the commencing of welding, the sensor output causes the circuitry 14 to drive the shutter 10 to the dark state blocking a substantial amount of light transmission from reaching the eyes 3 and, thus, providing eye protection. The light being blocked may be visible light, infrared light, and/or ultraviolet light. Reference to light herein means electromagnetic energy in the respective wavelength ranges indicated. Thus, in response to the occurrence of a specified light condition at the front or outside 15 of the welding lens cartridge assembly 12, the shutter 10, sensor 13 and circuitry 14 cooperate to protect the eyes 3 at the back 16 of the assembly 12 inside the helmet 1.

Referring to FIG. 2, the back side 16 of the welding lens cartridge assembly 12 is illustrated. The shutter 10 is mounted in a housing 20 of the assembly 12. The housing may be plastic, metal or some other material that provides suitable support structure for the lens holding it in place and also providing suitable mounting or connection in an opening 21 (FIG. 1) in the welding helmet shell 4. When the shutter 10 is in the clear state, a person can see directly through the shutter to view the environment external of the welding helmet 1. However, when the shutter 10 is in the dark state, preferably light transmission is blocked substantially, and easy viewing is limited to very bright areas, such as the area in close proximity to the place where welding is occurring and welding light is being developed. Preferably the welding helmet shell 4 and the cartridge assembly housing 20 are relatively non-transparent, most preferably not transparent at all, to block light transmission. Therefore, the only light received by the eyes 3 would be that passing through the shutter 10.

In FIG. 2 the shutter 10, which is described in further detail below, is shown mounted in the housing frame 20 of the welding lens cartridge assembly 12. At the front side 15 of the assembly 12 in front of the shutter 10 and mounted in the housing frame 20 is a protective cover plate 23. The cover plate 23 may be optically transparent or it may be tinted, partially reflective, include a band pass filter, or have some other desired optical characteristics. An important function of the cover plate 23 is to protect the front of the shutter from dirt, grease, finger prints, scratches, and/or other damage or abuse. If desired, the cover plate 23 may be of the type that can be removed and replaced, for example, in case it were to become scratched to an extent that it interferes with viewing through the assembly 12. Exemplary cover plates are known, and an example is presented in U.S. Pat. No. 5,377,032. As illustrated, the light sensor 13 is located between the shutter 10 and cover plate 23 where light due to welding and/or the ambient environment can reach the sensor while the sensor also is protected by the cover plate.

At the back side 16 of the welding lens cartridge assembly 12 behind the shutter 10 and mounted in the housing frame 20 is the deflectable cover plate 7, which is associated with the switch system 6. The deflectable cover plate 7 also may be of clear or transparent material, such as plastic or glass, as is the cover plate 23. The cover plate 7 also may have other characteristics, such as band pass filter, tinting, etc. characteristics. The cover plate 7 is able to be deflected to operate the switch system 6. In this regard, the cover plate 7 may be somewhat flexible and so mounted in the housing frame 20 that it can be deformed by pressing on it to operate the switch system 6. As an alternative the cover plate 7 may be mounted in the housing frame 20 for slight movement in response to such force or pressure as it is pressed thereby to operate the switch system 6.

As is illustrated in FIGS. 2–5, the switch electrodes 8 actually include two pairs of switch electrodes 8', 8". There may be fewer or more pairs of switch electrodes. The switch electrode pair 8', for example, includes a pair of switch contacts, 24a, 24b which are located on the support 9. The switch contacts 24a may be connected electrically by engagement therewith by the switch electrode 8", which operates as a switch pad or contact pad. The switch contacts 24a, 24b may be electrically coupled in the circuitry 14 and upon connection thereof by the switch pad electrode 8" effects a setting of an operational characteristic of the circuit and/or of the shutter 10 or may effect another function, as may be desired.

The support 9 may be a circuit board or the like, an example being a rigid or flexible printed circuit board. At least some of circuitry 14 may be printed on or otherwise mounted on or attached to the circuit board 9. The switch contacts 24a, 24b may be printed or otherwise formed on, mounted on or attached to the circuit board 9. A rib 25 in connection with other walls or members of the housing 20 form a receiving area 26 for relatively secure positioning and retention of the circuit board 9 in the housing, as is seen in FIG. 3, for example.

The shutter 10 and display 11 are positioned and retained in another receiving area 27 of the housing 20, as also is seen in FIG. 3.

A switch spacer 28 and a flexible overlay material 29 are positioned between the support 9 and the cover plate 7. The spacer 28 has one or more opening areas 28a generally circumscribing the area of each of the switches 8, to provide a space where the contact pad 8" of respective switch electrode pairs can be moved into engagement with respective switch contacts 24a, 24b. In the illustration of FIGS. 2–4, there are two such openings 28a. Other portions 28b of the switch spacer 29 have a sufficient thickness to space the flexible overlay material 29 and the cover plate 7, and, thus, the respective contact pads 8", from the circuit board support 9 and switch contacts 24a, 24b. The switch spacer 28 may be engaged directly with the circuit board support 9 or may be spaced away from it by engagement with the housing frame 20. Preferably the switch spacer 28 is made of electrically non-conductive material to avoid causing a short circuit to any of the circuitry or components of the circuitry 14.

The flexible overlay 29 may have an optically transparent characteristic to permit viewing therethrough. The flexible overly material preferably is electrically non-conductive so that the contact pads 8" are electrically isolated from each other. Alternatively, if desired, the contact pads may be mounted on insulating material and, therefore, the material of the flexible overlay 29 is made may be conductive or non-conductive.

In making the assembly 12, the circuitry 14 is attached to the shutter 10 and display 11, and all are assembled in the housing 20. The cover plate 23 is installed in the housing 20. The spacer 28 and flexible overlay 29 are positioned relative to the housing 20, circuitry 14 and shutter 10 in the manner illustrated in FIG. 3, for example. The cover plate 7 is installed in the housing 20 engaged with the flexible overlay 29. The assembly 12 then can be installed in the welding helmet shell 4.

Use of the respective switches 8 is depicted in FIGS. 4 and 5. The switch spacer 28 ordinarily spaces the switch pads 8" away from respective switch contacts 24a, 24b. However, when desired to close one of the switches 8, one may press a finger or tool against the cover plate 7 causing it and the flexible overlay 29 to deflect and to move the switch pad 8" into the opening or space 28a, as is shown in FIG. 5, to engage a respective pair of switch contacts 24a, 24b, closing an electrical circuit therebetween and causing an operative effect, such as stepping through a sequence of conditions, of the circuitry 14 that controls one or more operational characteristics of the shutter 10 of the assembly 12. Upon releasing of the pressing action, the cover plate 7, flexible overlay and switch pad 8" return to the respective locations and conditions illustrated in FIG. 4 due to the flexibility/possible resilience of the flexible overlay 29 and/or the cover plate 7 and/or due to the force exerted by the portion 28b of the spacer 28.

Figure 6:
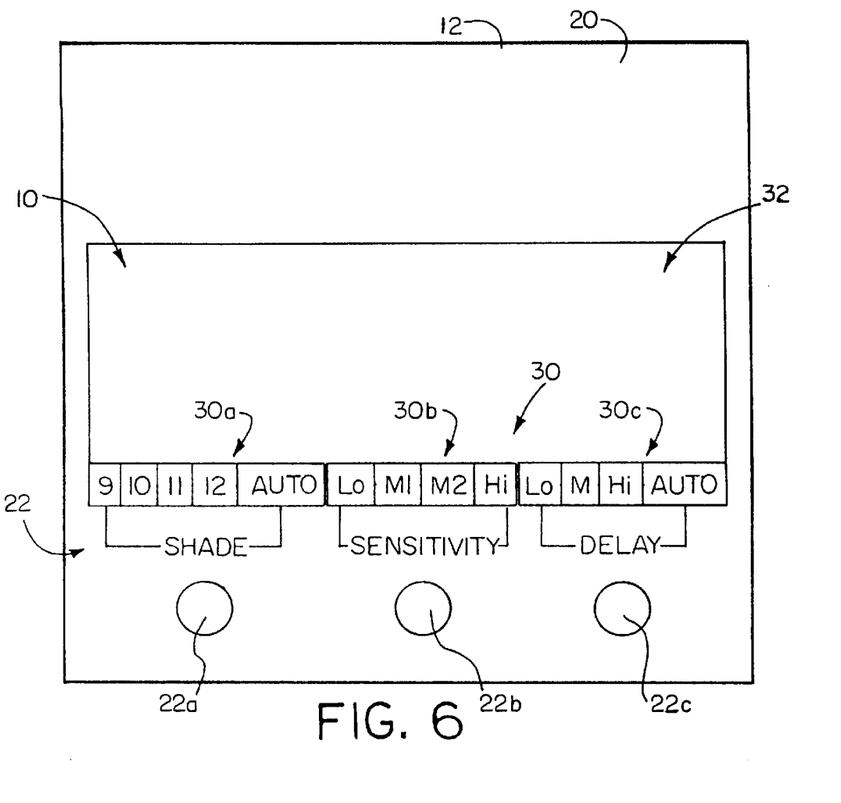
FIG. 6 is a back elevation view of the welding lens cartridge assembly of the welding helmet in FIG. 1.

In FIG. 6 at the bottom of the shutter 10 is illustrated plural indicia 30 of the integral indicator 11 (FIG. 1). The indicia 30 are arranged in three groups 30a, 30b, and 30c, each group representing respective values or functions of operating characteristics of the shutter 10 and circuitry 14. For example, the indicia 30a are labeled respectively 9 through 12 and "Auto". The numerical values identify respective shade numbers, which represent respective dark states of the shutter. When the shutter 10 and circuitry 14 are set to operate at shade 9, which is a known light transmission value, then in the dark state the shutter 10 assumes a light blocking/transmitting characteristic of a shade 9 lens. Each of the shades 9 through 12 can be set for the shutter 10 by stepping the circuitry 14 in response to sequential operation of one of the switches 22, say switch 22a. For example, for a given shade number level, the circuitry 14 would be adjusted to apply a particular voltage to respective electrodes of liquid crystal cells included in the shutter to apply an electric field of corresponding magnitude to the liquid crystal to obtain the desired shade number value. In the "Auto" shade operating characteristic, the circuitry 14 may adjust shade depending on one or more other characteristics, such as a comparison between ambient brightness and brightness of light emitted during welding, specific ambient light conditions, etc. In operation of the integral indicator 11, only one of the respective indicia 30a would be visible at a particular time to indicate the particular shade operating characteristic of the shutter 10 as set in the circuitry 14 by appropriate operation of the switch 22a.

Similarly, switches 22b, 22c can be operated to sequence the circuitry 14 through respective sensitivity adjustments and through respective delay adjustments. The sensitivity adjustments include a low sensitivity, high sensitivity, and two intermediate sensitivity levels. Sensitivity is the responsiveness of the circuit to a change in light conditions detected by the sensor 13 so as to cause the circuitry to operate the shutter 10 from dark condition. The delay switch 22c may be operated to step the circuitry 14 sequentially through low, medium, high and automatic delay operational characteristics for the shutter 10. When the delay is low, the circuitry 14 operates the shutter 10 to dark to clear state relatively promptly after the cessation of welding has been detected by the sensor 13, and when the delay is high, that time period is longer. In the automatic delay mode, the circuitry 14 may determine automatically the delay period, for example, based on external conditions detected by the sensor 13, such as ambient lighting conditions, brightness of the welding light, a comparison thereof, etc.

Figure 7:
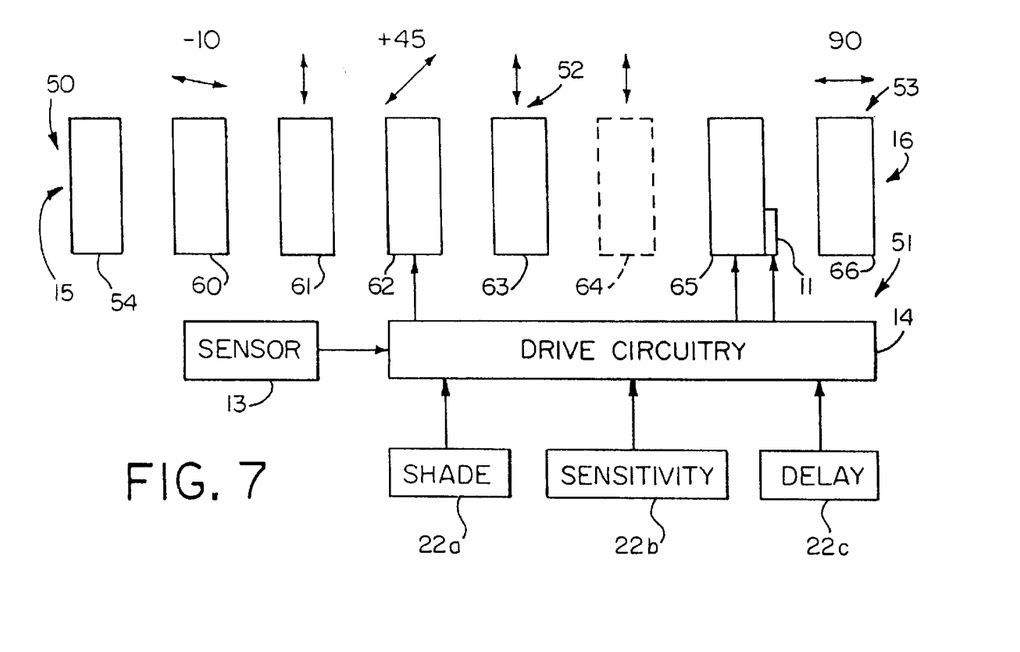
FIG. 7 is a schematic illustration of a series of optical components useful in the welding lens assembly of the invention.

Turning to FIG. 7, the shutter 10 with the integral indicator 11 and associated circuitry 14 are shown schematically in greater detail. Construction, use and operation of the shutter 10 is described with respect to protecting the eyes 3 during welding, and, therefore, the components of the shutter will be referred to below as a welding lens or simply as a lens, which is designated 50. However, the lens 50 and features thereof may be used for other eye protection, etc. purposes, and the integral indicator may be used in other devices, too. For convenience, the lens 50 in combination with the sensor 13, circuitry 14 and various adjustment controls, such as switches 22a, 22b, 22c, will be referred to here collectively as the welding lens assembly or simply as lens assembly 51. It will be appreciated that the components used in the lens assembly 51 are exemplary, and that other components may be used to provide a desired amount and type of optical protection, such as eye protection from bright light occurring in welding or in some other type of operation or as a result of some other type of phenomenon.

The integral indicator 11 is integral with a portion of the lens 50 and is operable to display to a user respective indicia 30 representing one or more operational characteristics of the lens assembly 51. In the embodiment described the indicator is near the bottom of the viewing area 30 of the lens 50. However, if desired, the indicator 11 may be positioned at another location in the lens 50. With the indicator 11 at or near the bottom of the lens 50, it will not interfere with (or at least it will only minimally interfere with) the viewing area 30 and field of view seen by the eyes 3 when the helmet 1 is worn (FIG. 1). However, the indicator 11 easily may be viewed when the helmet is not being worn and the lens 50 is not in the dark state. Additionally, as will become evident from the description below, the indicator 11 preferably does not interfere with the light blocking function of the lens 50.

The optical components of the welding lens 50, which are shown on FIG. 7, include a pair of liquid crystal shutters 52, 53 and input band pass filter 54. An additional output band pass filter or simply a protective transparent plate or filtering plate (not shown) may be provided at the front 15 or back 16 of the welding lens 50 for filtering function and/or for protection from damage, such as by scratching or the like.

The liquid crystal shutters 52, 53 and the band pass filter 54 are in optical series. The band pass filter 54 blocks from transmission to the liquid crystal shutters electromagnetic radiation (light) in the infrared and ultraviolet ranges. An exemplary band pass filter includes a hot mirror, such as that sold under the trademark Coolbeam™ and hot mirror by Optical Coating Laboratory, Inc. of Santa Rosa, Calif. with an additional coating of indium tin oxide to provide adequate filtering of infrared energy to 2,000 nm (nanometers). An example of such a band pass filter is described in copending, commonly assigned U.S. patent application Ser. No. 08/105,734, filed Aug. 11, 1993.

The first liquid crystal shutter 52 includes in optical series an input polarizer 60, a wave plate 61, a liquid crystal cell 62, and an output polarizer (sometimes referred to as an analyzer) 63. The polarizer 60 and analyzer 63 preferably are plane (linear) polarizers. The wave plate 61 may be a quarter wave plate for green light, although it may be a quarter wave plate for other than green light or for more than green light, and, if desired, the wave plate 61 may be other than a quarter wave plate. The liquid crystal cell 62 is a birefringent cell, such as a surface mode liquid crystal cell or pi-cell as is described in various of the aforementioned patents. The wave plate 61 compensates for residual retardation in the birefringent liquid crystal cell 62 as is described below. The alignment directions of the transmission axis for each polarizer 60, 63 and the axis of the wave plate 61 and the rub direction of the liquid crystal cell 62 are represented by arrows above the respective components.

The liquid crystal shutter 52 operates in response to voltage supplied by the drive circuitry 14. When the sensor 13 is not detecting welding and the drive circuitry 14 operates the liquid crystal cell 62 at relatively low voltage (for example, RMS voltage, DC or AC voltage), the liquid crystal cell provides optical phase retardation for incident polarized light to deliver as an output to the polarizer 63 light that is plane polarized substantially in the direction of the transmission axis of the polarizer 63. Therefore, the shutter 52 transmits a relatively maximum amount of light. In contrast, when the sensor 13 is detecting welding and the drive circuitry 14 supplies a relatively high voltage to the liquid crystal cell 62, the amount of retardation provided by the liquid crystal cell is reduced so that the output provided the polarizer 63 is plane polarized light having an electric vector that is in a direction other than the direction of the transmission axis of the polarizer 63. In an embodiment of the invention, at maximum voltage provided by drive circuitry 14 to liquid crystal cell 62, the direction of plane polarized light output from the liquid crystal cell is substantially perpendicular to the direction of the polarizer 63 transmission axis. However, at a slightly reduced, but nevertheless relatively high, voltage, the direction of the plane polarized light remains substantially perpendicular or is only slightly deviating from perpendicular to the direction of the transmission axis of polarizer 63. As a result of such perpendicular or nearly perpendicular orientation of the polarized light incident on the polarizer 63, transmission thereof will be substantially blocked by the polarizer 63.

The liquid crystal shutter 52 is set up, i.e., the axial directions and respective values or parameters of the components 60–63 are so selected and arranged, that some light will be transmitted through the polarizer 63, even in the dark state, so that the person using the welding helmet 1 including the lens 50 will be able to see the welding operation while the eyes are protected from bright light. Also, as is known, most plane polarizers tend to leak some light, and such leakage by polarizer 60 of light that is not polarized in the direction of transmission axis thereof and leakage by polarizer 63 permits such transmission and viewing capability. However, the amount of light transmitted through the polarizer 63 when the lens 50 is in dark mode also can be adjusted by varying the voltage applied to the liquid crystal 62. By changing that voltage the amount of retardation applied to the light transmitted through the liquid crystal cell 62 can be changed, and, accordingly, the respective shade numbers identified by indicia 30a can be achieved by the welding lens 50.

Liquid crystal shutter 53 is in optical series with liquid crystal shutter 52 and band pass filter 54. Liquid crystal shutter 53 includes an input polarizer, which may be polarizer/analyzer 63 mentioned above or may be a separate polarizer 64, a liquid crystal cell 65, and an analyzer or output polarizer 66. Polarizers 64 and 66 are plane (linear) polarizers, and the relative directions of the transmission axes are identified by arrows above each polarizer. Although polarizer 64 may be optional, use may increase contrast ratio, improve efficiency and optimize performance of lens 50, especially if leakage light through polarizer 63 includes unpolarized light. Liquid crystal cell 65 is a twisted nematic liquid crystal cell. Such liquid crystal cell includes a pair of substrates on which electrodes are formed and between which nematic liquid crystal material is located. Absent a suitable electric field applied across a liquid crystal material by the electrodes, the liquid crystal material tends to rotate the plane of polarization of incident plane polarized light by an amount determined by the relative rub or alignment directions at the internal surfaces of the substrates; and in response to a suitable electric field, the liquid crystal material aligns with the field and transmits plane polarized light without altering (or substantially without altering) plane of polarization.

In operation of welding lens 50 in clear state, it is intended that a relatively maximum amount of light is transmitted to eyes 3. Accordingly, liquid crystal shutters 52, 53 transmit a relatively maximum amount of light. More specifically, band pass filter 54 performs its filtering function and transmits to input polarizer 60 at least some light that is in the visible wavelength range. Polarizer 60 polarizes that light and passes that plane polarized light to wave plate 61, and light from wave plate 61 is incident on birefringent liquid crystal cell 62. In clear state of lens 50, liquid crystal cell 62 provides maximum optical phase retardation and rotates plane of polarization of light incident thereon so that the plane of polarization is substantially parallel to the direction of the transmission axis of analyzer 63 for transmission thereby. Plane polarized light from polarizer 63 is directed to the second liquid crystal shutter 53. In the second liquid crystal shutter 53, plane polarized light from the analyzer 63 is transmitted directly to or via plane polarizer 64 to twisted nematic liquid crystal cell 65. If polarizer 64 is used, it serves as the input polarizer to liquid crystal shutter 53, and if not used, then the analyzer 63 serves as the input polarizer to the liquid crystal shutter 53. The liquid crystal cell 65 is in the twisted mode so that it rotates the plane of polarization of the incident light thereto to a direction that is parallel to the alignment direction of the transmission axis of the analyzer 66. Accordingly, the light is transmitted through the analyzer 66 as output light at the back 16 of the lens 50 for viewing by the eyes 3.

During operation of the welding lens 50 in the clear state, the drive circuitry 14 may operate the indicator 11 to present a display of respective indicia 30 for viewing by the user before placing the welding helmet on the head 2. While the indicia are displayed, the user may operate one or more of the respective switches 22a, 22b, 22c (or other ones, if used) to set desired operational characteristics for the welding lens assembly 51. The indicator 11 may include transmissive or reflective display portions and which can be seen clearly when the lens 50 is in the clear state.

The birefringent liquid crystal cell 62 in the liquid crystal shutter 52 may have residual birefringence even when it is driven at maximum voltage. The wave plate 61 is provided in the liquid crystal shutter 52 to compensate for such residual birefringence, and the alignment of the transmission axis for the input polarizer 60 also is set to cooperate with the wave plate 61 and with the operating characteristics of the birefringent liquid crystal cell in the respective clear and dark states so that plane polarized light will be selectively transmitted or blocked by the polarizer 63 in response to the actual voltage or RMS voltage applied by the drive circuitry 14 and the corresponding electric field developed in the birefringent liquid crystal cell 62. Such compensation provided by the wave plate 61 and alignment of the input polarizer 60 are described in various of the aforementioned patents and patent applications, such as, for example, in the '688 patent.

In operation of welding lens 50 in dark state, upon welding or some other conditions occurs that is detected by the sensor 13 to cause a drive circuitry 14 to operate the welding lens 50 in the dark state, the following occurs. The drive circuitry 14 drives the liquid crystal shutters 52, 53 to the dark states. The birefringent liquid crystal cell 62 is driven at a relatively high voltage so that the liquid crystal material therein does not retard (or rotate) the polarized light transmitted therethrough, and with compensation provided by the wave plate 61 and the alignment of the input polarizer 60, the result is substantial blocking of light transmission by the analyzer 63. Polarized light transmitted by the polarizer 63 is delivered directly or via the polarizer 64 to the twisted nematic liquid crystal cell 65. The drive circuitry 14 also operates the twisted nematic liquid crystal cell 65 driving it to a state that it does not rotate plane of polarization. Therefore, the light incident on the analyzer 66 is plane polarized in the direction that is perpendicular to the direction of the transmission axis of such analyzer 66, and the analyzer 66 will block a substantial amount of such light.

The percentage of light blocked by the liquid crystal shutter 53 in the dark state ordinarily will remain relatively constant. However, the percentage of light blocked by the liquid crystal shutter 52 may be altered by changing the voltage applied to the liquid crystal shutter 62; such alteration allows the lens 50 to be operated at different respective shade numbers. Such shade numbers can be controlled by operating the switch 22a to change operational characteristics of the circuitry 14, for example, by switching the values of various resistors in the circuit, etc. It will be appreciated that operation of the welding lens 50 to provide a relatively low shade number requires less voltage and power from the drive circuitry 14 and the power source therefor, and a higher shade number ordinarily will require a higher voltage and more power, for example, to drive the birefringent liquid crystal cell 62. The sensitivity and delay operating characteristics of the welding lens assembly 51 can be similarly adjusted by operating the switches 22b, 22c.

An advantage to the combination of a birefringent liquid crystal shutter 52 and a twisted nematic liquid crystal shutter 53 in optical series in the welding lens 50 is the complimentary response times and voltage requirements. For example, a twisted nematic liquid crystal shutter 53 ordinarily does not require power in the twisted state (in this case the clear state) and requires less voltage and power to operate it driving it to the "untwisted" and in this case, dark, state than the voltage requirements for a birefringent liquid crystal shutter. However, operation of the twisted nematic liquid crystal shutter ordinarily is slower than that of a birefringent liquid crystal shutter. Therefore, upon the occurrence of welding and detection of the welding light by the sensor 13, the drive circuitry 14 provides outputs to drive the liquid crystal cell 62, 65 to dark state. The birefringent liquid crystal cell takes more voltage and operates faster than the twisted nematic liquid crystal cell 65 and, therefore, promptly darkens the welding lens 50. If desired, the drive circuitry 14 may compensate for the slower operation of the twisted nematic liquid crystal cell 65. In such case the circuitry 14 initially supplies to the birefringent liquid crystal cell 62 a voltage larger than necessary to achieve the desired shade number for the lens 50 so that the liquid crystal shutter 52 switches to dark state very fast and provides acceptable prompt eye protection. However, after the twisted nematic liquid crystal cell 65 has achieved its dark state, the voltage to the birefringent liquid crystal cell 62 can be reduced so that the liquid crystal shutters 52, 53 operating an optical series provides a desired shade number and eye protection.

Figures 8, 9:
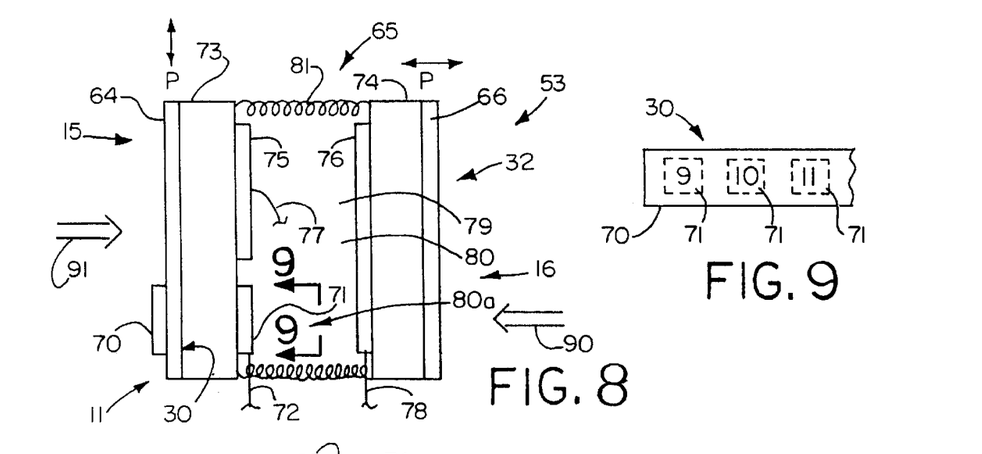
FIG. 8 is a fragmentary side elevation view of one of the liquid crystal light shutters of the welding lens of FIG. 7 including an integral reflective indicator.
FIG. 9 is a back elevation view of the shutter indicia looking generally in the direction of the arrows 9—9 of FIG. 8.

In FIGS. 8 and 9 is illustrated one embodiment of indicator 11 integral with the twisted nematic liquid crystal cell 65 of the liquid crystal shutter 53. The indicator 11 is a reflective type and it includes the indicia 30 printed on a reflective sheet or support 70. An example of a reflective support and display including a reflector is disclosed in U.S. Pat. No. 3,881,809. In FIG. 9 three shade numbers of the indicia 30a (FIG. 6) are depicted as examples; however, all of the indicia 30 may be printed on the support 70. The support 70 may extend across part or all of the width of the light shutter 65 preferably out of the viewing area 30. The indicator 11 also includes a plurality of transparent electrode segments 71, which are aligned in overlying relation to respective indicia, as is shown in FIG. 9. Each electrode segment 71 may be indium tin oxide or some other transparent electrode material, and each is connected by a respective lead, conductor or the like 72 to the drive circuitry 14 for selective energization (by application or not of a voltage) to cause viewing of a respective one of the indicia while light to others is blocked and they would not be seen.

Aside from the indicator 11, the liquid crystal cell 65 may be essentially a conventional twisted nematic liquid crystal cell. Such a liquid crystal cell includes a pair of substrates, such as glass plates, 73, 74, transparent electrodes 75, 76 on the respective substrates, electrical leads 77, 78 for connecting the respective electrodes to the drive circuitry for energization (application of a voltage) thereto, and liquid crystal material 79 in the space 80 between the substrates. A seal 81 seals the perimeter of the liquid crystal cell 65 to retain the liquid crystal material 79 in the space 80. The inner surfaces of the substrates 73, 74 and/or the electrodes 75, 76 have a surface treatment, for example, by rubbing, deposition, or some other technique, to align the liquid crystal material 79 with respect to those surfaces. In an exemplary case the alignment at one surface is relatively perpendicular to the alignment at the opposite surface. When the liquid crystal material 79 is of the nematic type (or is operationally nematic in that it has characteristics allowing it to operate like nematic liquid crystal), the liquid crystal aligns according to the treatment at the respective surfaces and will have a twist from one surface to the other. However, in response to application of suitable electric field input across the liquid crystal material, the liquid crystal material tends to align with the field. In the former case the liquid crystal material will rotate the plane of polarized light transmitted through it, and in the latter case the liquid crystal material will not affect the direction of polarization of the light transmitted through it, as is conventional.

In the indicator 11 the electrode segments 71 or the substrate 73 proximate those electrode segments also have surface treatments similar to that at the electrode 75 or rest of the substrate 73 surface as described above. Therefore, the liquid crystal material 79 in the space 80a between the electrode segment 71 and the electrode 76 also is in a twisted state in the absence of electric field or aligns with the electric field when a suitable voltage is applied between the respective electrode segment 71 and the electrode 76.

In operation of the indicator 11, light 90 is directed from the back 16 of the welding lens cartridge assembly 12 to the liquid crystal light shutter 53. The light is polarized by the polarizer 66 and is directed into the liquid crystal cell 65. At those areas where a suitable voltage is applied between a respective electrode segment 71 and the electrode 76, the electric field created there causes alignment of the liquid crystal material with the field so that no change in polarization direction occurs, and the light will be blocked from further transmission by the polarizer 64. However, where there is no electric field applied between a respective electrode segment 71 and the facing portion of the electrode 76, the liquid crystal material will remain twisted and will rotate the plane of polarization of the light transmitted therethrough. Accordingly, such light will be transmitted through the polarizer 64, will illuminate the reflective substrate 70 and respective one of the indicia thereof located in alignment with the then deenergized electrode segment 71. The light reflected by the reflective substrate 70 including the respective illuminated one of the indicia passes in a reverse direction back through the liquid crystal light shutter 53 for viewing by the user. More specifically, the reflected light is transmitted through the polarizer 64, the plane of polarization is rotated by the liquid crystal material in the space 80a, and the light is transmitted through the polarizer 66 for viewing. Similar operation is effected for the other portions of the indicator 11.

When the welding helmet 1 is positioned on the head of a user and welding is detected by the sensor 13, for example, and the lens 50 is driven to the dark state by the drive circuitry 14, electric field is supplied across all the liquid crystal material 79 in the liquid crystal cell 65, including that liquid crystal material not only in the space 80 but also that in the space 80a. Therefore, therefore, light blocking function will be provided by the entire liquid crystal shutter 53 including the integral indicator 11.

Another embodiment of an indicator 11a, which is similar to the indicator 11 described above, is illustrated in FIGS. 10 and 11. The indicator 11a is integral with a liquid crystal cell 65 that is part of a liquid crystal light shutter 53, which were described above. However, in the embodiment of FIG. 10, the indicator 11a is a transmissive one rather than a reflective one. More specifically, the indicator 11a includes electrode segments 71 that can be selectively energized from the drive circuitry 14 or not energized thereby to determine whether light 91 from the front 15 of the welding lens cartridge assembly will be transmitted through respective indicia 30. The indicia 30 may be painted, printed or otherwise formed on or applied to a substrate 70a shown in FIG. 11. Such substrate may be clear film, such as plastic, Mylar or some other material, and the indicia may be respective numbers, letters or symbols applied thereto and able to block light to provide information. Alternatively, the substrate 70a may be a light blocking material and the indicia may be transparent portions thereof.

Figures 10, 11:
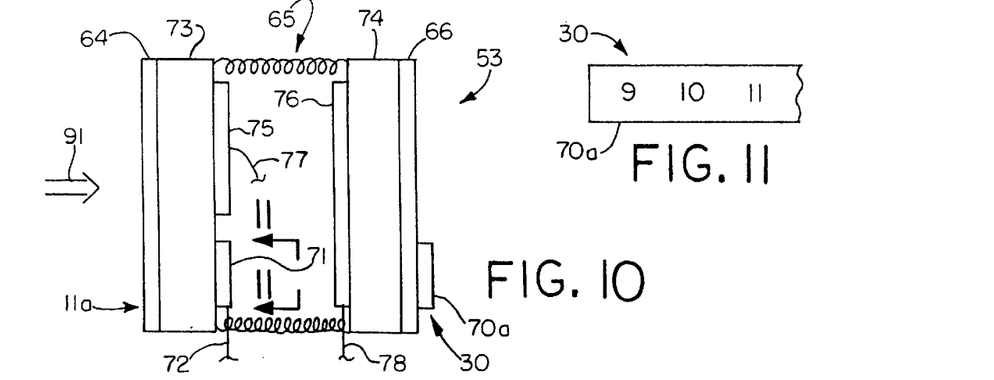
FIG. 10 is a fragmentary side elevation view of one of the liquid crystal shutters of the welding lens of FIG. 7 including an integral transmissive indicator.
FIG. 11 is a back elevation view of the indicia looking in the direction of the arrows 11—11 of FIG. 10.

The liquid crystal cell 65 and light shutter 53 of FIG. 10 operate in the manner described above, for example, with respect to FIG. 8. The indicator 11a is operable in response to voltage applied by the drive circuitry 14 to respective electrode segments 71 and electrode 76 (or not applying voltage thereto) to determine whether light 91 is transmitted through a respective one or more of the indicia 30 on the substrate 70a. For example, in the absence of electric field between an electrode segment 71 and electrode 76, light 91 is polarized by the polarizer 64, is transmitted through the substrate 73 and through the respective electrode segment 71, has the plane of polarization rotated by the twisted liquid crystal material 79, and then is transmitted through the electrode 76, substrate 74, polarizer 66 and finally through the effectively overlaying one of the indicia, thereby illuminating the indicia for viewing thereof. In response to application of voltage between an electrode segment 71 and electrode 76, though, the liquid crystal material 79 therebetween will align with the field and will not rotate the plane of polarization of polarized light transmitted therethrough; and, accordingly, light 91 is blocked by the polarizer 66 and will not illuminate the indicia 30.

It will be appreciated that other means may be used to form the respective indicia 30, such as, for example, electrode portions of the electrode segments 71, either in a light transmissive or light reflective type display arrangement, such as are described above and in the two U.S. Pat. Nos. 3,731,986 and 3,881,809 mentioned above.

Figure 12:
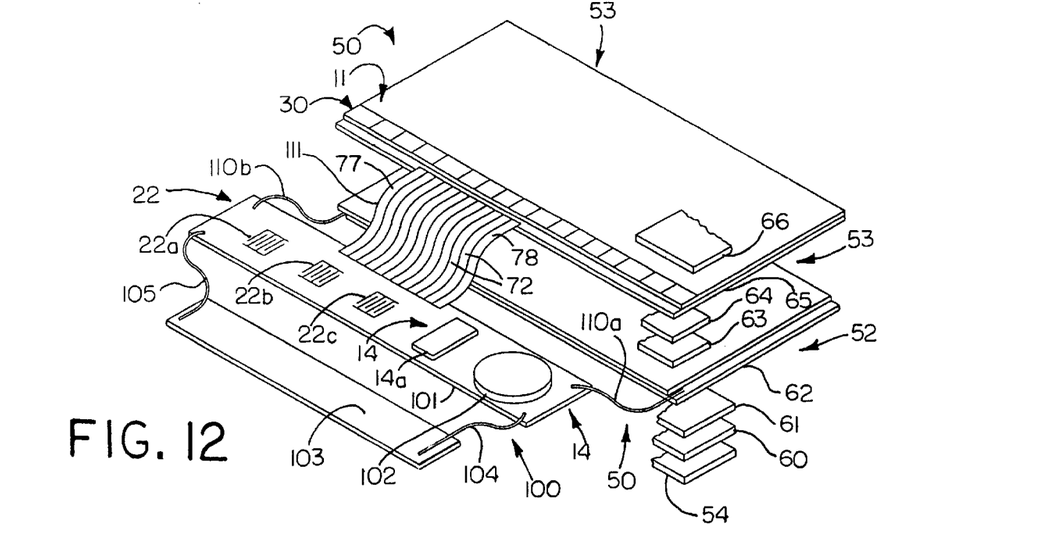
FIG. 12 is a fragmentary isometric view of the welding lens assembly of FIG. 7 including the associated drive circuitry.

In FIG. 12 the drive circuitry 14 is shown mounted on a circuit board 101 or other type of support. The power source 100 includes a battery 102, such as a lithium ion battery, or other electrical energy storage device. Additionally, the power source may include a solar cell 103 or other photoelectric type of device which is mounted in the welding lens cartridge assembly 12 for exposure to ambient light and/or to the welding light and in response to such light develops electrical energy to recharge the battery 102 and/or directly to supply electrical power to the drive circuitry 14. Electrical leads 104, 105 connect the solar cell 103 to electrically conductive traces (not shown) on the circuit board 101 for connection to the battery 102 and/or directly to the drive circuitry 14.

As shown in FIG. 12, the drive circuitry 14 is embodied in a single integrated circuit 14a. There may be additional resistors, capacitors, inductors, and/or other solid state or other components associated with the integrated circuit 14a which are mounted elsewhere on the circuit board 101 and connected to the integrated circuit 14a by conductive traces or the like, as is conventional. However, in an embodiment of the invention as much as possible of the drive circuitry 14 is embodied entirely within the integrated circuit 14a, for example, for compactness, ease of construction, etc. The circuitry 14 may be the same as or of the type disclosed in one or more of the above patents and applications.

The drive circuitry 14 is connected to the birefringent mode liquid crystal cell 62 by respective electrical leads or other connections 110a, 110b, which are collectively designated 110 in the drawing of FIG. 7. The connections 72, 77, and 78 from the drive circuitry 14 to the twisted nematic liquid crystal cell 65, including the integral indicator 11, are included in a ribbon cable connector 111 or other multiconductor connector device. The connections 77, 78 are to the respective electrodes 75, 76; and a plurality of connections 72 are proved leading, respectively, to the respective electrode segments 71 do cause display of respective operating characteristics or conditions by the indicator 11.

Therefore, in response to the settings of the drive circuitry 14 under control of the respective switches 22, the drive circuitry may deliver appropriate voltages to respective electrode segments 71 causing the appropriate display of operating characteristics for the welding lens assembly 51 for viewing by the user. After having made the desired settings of the operating characteristics, the user may put on the welding helmet. While welding or other bright light condition is not detected by the sensor 13, the drive circuitry 14 would operate the welding lens 50 to the clear state. Upon detecting a light condition for which eye protection is desired, the sensor output to the drive circuitry 14 causes the drive circuitry to operate the welding lens 50 to dark condition according to the operating conditions or characteristics set in the circuitry by the switches 14.

Statement of Industrial Applicability

In view of the foregoing it will be appreciated that the present invention may be used to provide eye protection and a method of eye protection for a welder, to select operating characteristics of the welding lens assembly, and to display or to indicate those operating characteristics.

I claim:

1. An automatically darkening lens assembly, comprising a controllable light shutter for controlling transmission of light for viewing therethrough, a circuit for operating said light shutter and affecting operating characteristics thereof, a switch operable to select at least one of such operating characteristics, a display for displaying at least one of such operating characteristics, said display being positioned to permit substantially unobstructed viewing through said lens assembly, a support for mounting at least a portion of said switch, a cover plate overlying at least part of said light shutter and said circuit, said switch being operable in response to deflection of said cover plate.

2. A light shutter for a welding helmet, comprising a frame structure for an electro-optic shutter assembly, said frame structure having a front surface to be exposed to light and a back surface facing a viewer during welding operation, said shutter assembly including a display for displaying at least one of a plurality of operational modes of said shutter assembly, said display being positioned to permit substantially unobstructed viewing through said shutter assembly, a protective member covering at least a part of the back surface, switching means for controlling (an) a substantial portion of said operational modes of said electro-optic shutter assembly, said switching means being operable in response to pressure applied to said protective member.

3. A method for operating an auto-darkening welding lens including an operating circuit, comprising selecting an operational characteristic of the welding lens by setting a characteristic of the circuit, said setting comprising deflecting a mechanical member of the welding lens to operate a switch, placing a viewing portion of the welding lens before the eyes of the welder to provide a light shuttering operation for eye protection, and displaying at least one of a plurality of operating characteristics of the welding lens while permitting a substantially unobstructed view through said welding lens.

4. The method of claim 3, wherein the welding lens includes a light shutter and a cover plate, and said deflecting comprising deflecting the cover plate.

5. The method of claim 4, said deflecting of the cover plate comprising deflecting the cover plate to close a switch.

6. The method of claim 5, the welding lens including a plurality of switches, and said deflecting comprising deflecting the cover plate at respective portions thereof thereby to close respective switches.

7. The method of claim 6, comprising wherein operation of respective switches effect setting of respective operational characteristics of shade, sensitivity and delay.

8. The method of claim 7, further comprising (protecting the eyes of a welder using the an auto-darkening welding lens, including) using a display portion of the welding lens displaying such operating characteristic selected by operation of such switches, (placing a viewing portion of the welding lens before the eyes of the welder to provide a light shuttering operation for eye protection,) and darkening the display portion of the welding lens assembly when the viewing portion is darkened to protect the eyes of the welder.

9. A welding helmet having an automatically darkening lens assembly comprising a controllable light shutter for controlling transmission of light for viewing therethrough, a circuit for operating said light shutter and adjusting a plurality of operating characteristics thereof, (and) a plurality of switches each one of which is associated with and operable to adjust at least one of said operating characteristics of said light shutter, and a display associated with each of said switches for displaying an indicated value of said operating characteristic, said display being oriented with respect to said shutter to permit substantially unobstructed view through said shutter.

10. The helmet of claim 9 wherein said light shutter has a viewing portion, and wherein said display is integral with said viewing portion.

11. The helmet of claim 10 wherein said switches are operable from inside the helmet.

12. The helmet of claim 11 wherein said operating characteristics comprise shade, sensitivity, and delay of said light shutter, and said plurality of switches comprises three switches.

13. The helmet of claim 12 further comprising a protective member covering at least a part of said light shutter, and wherein said switches are individually operable in response to a deflection of said protective member.

14. The helmet of claim 13 wherein each of said switches is integrally mounted on a printed circuit board, said printed circuit board containing said operating circuit.

15. The helmet of claim 14 wherein said operating circuit darkens said display as it darkens said viewing portion.

16. A welding helmet having an automatically darkening lens assembly comprising a controllable light shutter for controlling transmission of light for viewing therethrough, a circuit for operating said light shutter and adjusting a plurality of operating characteristics thereof, and a display for displaying (the) an adjusted value of said operating characteristics, said display being integral with said light shutter and viewable through said light shutter by a wearer of said helmet, and said display permitting substantially unobstructed viewing through said shutter.

17. The welding helmet of claim 16 further comprising a plurality of switches integrally mounted with said light shutter, each one of which is associated with and operable to adjust at least one of said operating characteristics of said light shutter.

18. The welding helmet of claim 17 wherein said switches are operable from inside the helmet.

19. The welding helmet of claim 18 wherein said operating circuit darkens said display as it darkens said light shutter.

20. The welding shutter of claim 19 wherein said display includes a range of permissible values for each of said operating characteristics so that a user may select from among said permissible values.

\* \* \* \* \*

UNITED STATES PATENT AND TRADEMARK OFFICE
CERTIFICATE OF CORRECTION

PATENT NO. : 5,959,705
DATED : September 28, 1999
INVENTOR(S) : John D. Fergason

It is certified that error appears in the above-identified patent and that said Letters Patent is hereby corrected as shown below:

Column 16,
Line 3, after "controlling" delete "(an)".
Lines 30, 31 and 32, after "comprising" delete "(protecting the eyes of a welder using the an auto-darkening welding lens, including)".
Lines 34, 35 and 36, after "switching," delete "(placing a viewing portion of the welding lens before the eyes of the welder to provide a light shuttering operation for eye protection,)".
Line 43, after "therefor," delete "(and)".

Column 17,
Line 6, after "displaying" delete "(the)".

Signed and Sealed this

Twenty-seventh Day of December, 2005

JON W. DUDAS
*Director of the United States Patent and Trademark Office*